US007291592B2

(12) United States Patent
Gould et al.

(10) Patent No.: US 7,291,592 B2
(45) Date of Patent: Nov. 6, 2007

(54) METHOD FOR TREATING PATIENTS WITH MASSIVE BLOOD LOSS

(75) Inventors: Steven Gould, Highland Park, IL (US); Richard DeWoskin, St. Charles, IL (US); Marc Doubleday, Cary, IL (US); George Hides, Chicago, IL (US)

(73) Assignee: Northfield Laboratories, Inc., Evanston, IL (US)

( * ) Notice: Subject to any disclaimer, the term of this patent is extended or adjusted under 35 U.S.C. 154(b) by 312 days.

(21) Appl. No.: 10/678,927

(22) Filed: Oct. 3, 2003

(65) Prior Publication Data

US 2004/0067876 A1 Apr. 8, 2004

Related U.S. Application Data

(60) Provisional application No. 60/415,935, filed on Oct. 3, 2002.

(51) Int. Cl.
*A61K 38/16* (2006.01)
*A61K 35/14* (2006.01)

(52) U.S. Cl. .................. 514/6; 514/814; 514/832; 514/921; 514/930; 530/385; 530/402; 530/829; 424/529; 424/533

(58) Field of Classification Search .................. 514/6, 514/814, 832, 921, 930; 530/385, 402, 829; 424/529, 533
See application file for complete search history.

(56) References Cited

U.S. PATENT DOCUMENTS

| 4,826,811 | A | 5/1989 | Sehgal et al. |
|---|---|---|---|
| 5,084,558 | A | 1/1992 | Rausch et al. |
| 5,464,814 | A | 11/1995 | Sehgal et al. |
| 5,691,452 | A | 11/1997 | Gawryl et al. |
| 5,691,453 | A | 11/1997 | Wirtz et al. |
| 5,840,852 | A | 11/1998 | Rausch et al. |
| 5,895,810 | A | 4/1999 | Light et al. |
| 5,955,581 | A | 9/1999 | Rausch et al. |
| 6,150,507 | A | 11/2000 | Houtchens et al. |
| 6,271,351 | B1 | 8/2001 | Gawryl et al. |
| 6,288,027 | B1 | 9/2001 | Gawryl et al. |
| 6,323,320 | B1 * | 11/2001 | Sehgal et al. ............ 530/385 |
| 6,498,141 | B2 | 12/2002 | DeWoskin et al. |
| 2002/0065211 | A1 | 5/2002 | Jacobs, Jr. et al. |

OTHER PUBLICATIONS

Gould, S.A., et al., *The Life-Sustaining Capacity of Human Polymerized Hemoglobin when Red Cells Might Be Unavailable*, Journal of the American College of Surgeons, 195 (4): 445-455 (Oct. 2002).
Carson, J.L., et al., *Mortality and morbidity in patients with very low postoperative Hb levels who decline blood transfusion*, Transfusion, 42: 812-818 (Jul. 2002).
Moore, F.A., et al., *Trauma Resuscitation*, ACS Surgery- Principles & Practice, 31-61 (2002).
American College of Surgeons Committee on Trauma. Advanced Trauma Life Support Program for Physicians 1997 Instructional Manual, 6$^{th}$, ed. Chicago: American College of Surgeons; 98-117 (1997).
Farion, K.J., et al., *Changes in Red Cell Transfusion Practice among Adult Trauma Victims*, J. Trauma, 44(4):583-587 (1998).
Baker, J.B., et al., *Type and Crossmatch of the Trauma Patient*, J. Trauma, 50(5):878-881(May 2001).
DeFoe, G.R., et al., *Lowest Hematocrit on Bypass and Adverse Outcomes Associated with Coronary Artery Bypass Grafting*, Ann Thorac Surg., 71:769-776 (2001).
Wu, W.C., et al., *Blood Transfusion in Elderly Patients with Acute Myocardial Infarction*, New England Journal of Medicine, 345(17):1230-1236 (Oct. 2001).
Practice Guidelines for Blood Component Therapy: A report by the American Society of Anesthesiologists Task Force on Blood Component Therapy, Anesthesiology 84(3):732-747 (Mar. 1996).
Consensus Conference. Perioperative Red Blood Cell Transfusion, JAMA 260(18): 2700-2703 (Nov. 1988).
Gould, S.A., et al., *Fluosol DA-20 As A Red Cell Substitute in Acute Anemia*, New England Journal of Medicine, 314(26):1653-1656 (Jun. 1986).
Spence, R.K., et al., *Fluosol DA-20 in the treatment of severe anemia: Randomized, controlled study of 46 patients*, Critical Care Medicine, 18(11):1227-1230 (Nov. 1990).
Spence, R.K., et al., *Is Hemoglobin Level Alone a Reliable Predictor of Outcome in the Severely Anemic Patient?* The American Surgeon, 58(2):92-95 (1992).
Carson, J.L., et al., *Severity of Anaemia and Operative Mortality and Morbidity*, Lancet 1(8588):727-729 (Apr. 1988).
Carson, J.L, et al., *Effect of anaemia and cardiovascular disease on surgical mortality and morbidity*, Lancet, 348(9034):1055-1060 (Oct. 1996).
Viele, M.K., et al., *What can we learn about the need for transfusion from patients who refuse blood? The experience with Jehovah's Witnesses*, Transfusion 34(5):396-401 (1994).
Sehgal L.R., et al., *Polymerized pyridoxylated hemoglobin: A red cell substitute with normal oxygen capacity*, Surgery 95:433-438 (1984).
Amberson, W.R., et al.,*Clinical Experience with Hemoglobin-Saline Solutions*, J. Applied Physiology, 1(7):469-489 (Jan. 1949).
Brandt, J.L., et al., *The Effects of Hemoglobin Solutions on Renal Functions in Man*, Blood, 6:1152-1158 (1951).
Miller, J.H., et al., *The Effect of Hemoglobin on Renal Function in The Human*, Journal of Clinical Investigation, 30:1033-1040 (Jul. 1951).
Savitsky, J.P., et al., *A clinical trial of stroma-free hemoglobin*, Clinical Pharmacology Journal, 23(1):73-80 (Jan. 1978).
Carmichael, F.J., et al., *A phase I study of oxidized raffinose cross-linked human hemoglobin*, Crit Care Med, 28(7):2283-2292 (2000).
Kasper, S.M., et al., *Effects of a Hemoglobin-Based Oxygen Carrier (HBOC-201) on Hemodynamics and Oxygen Transport in Patients Undergoing Preoperative Hemodiulution for Elective Abdominal Aortic Surgery*, Anesth Analg, 83:921-927 (1996).

(Continued)

*Primary Examiner*—Jon Weber
*Assistant Examiner*—Abdel A Mohamed
(74) *Attorney, Agent, or Firm*—McDonnell Boehnen Hulbert & Berghoff

(57) ABSTRACT

Methods for treating a mammal suffering from massive blood loss comprising administering to the mammal a polymerized hemoglobin solution.

13 Claims, 4 Drawing Sheets

OTHER PUBLICATIONS

LaMuraglia, G.M., et al., *The reduction of the allogenic transfusion requirement in aortic surgery with a hemoglobin-based solution*, J. Vascular Surgery, 31(2):299-308 (Feb. 2000).

Sloan, E.P., et al., *Diaspirin Cross-Linked Hemoglobin (DCLHb) in the Treatment of Severe Traumatic Hemorrhagic Shock*, JAMA 282:1857-1864 (Nov. 1999).

Gould, S.A., et al., *Clinical Utility of Human Polymerized Hemoglobin as a Blood Substitute afterAcute Ttrauma and Urgent Surgery*, J. Trauma 43(2):325-332 (Aug. 1997).

Gould, S.A., et al., *The First Randomized Trial of Human Polymerized Hemoglobin as a Blood Substitute in Acute Trauma and Emergent Surgery*, J Am Coll Surg 187(2):113-122 (Aug. 1998).

Vengelen-Tyler, V., American Association of Blood Banks Technical Manual. 13th ed., Bethesda (MD): American Association of Blood Banks, p. 389-396 (1999).

Huston, P., et al., *Withholding Proven Treatment in Clinical Research*, New England Journal of Medicine 345(12):912-914 (Sep. 2001).

Emanuel, E.J., et al., *The Ethics of Placebo-Controlled Trials- A Middle Ground*, New England Journal of Medicine, 345(12):915-914 (Sep. 2001).

Carson, J.L, et al., *Mortality and morbidity in patients with very low blood counts who decline blood transfusion*, Transfusion, 42:812-818 (Jul. 2002).

Reiner, A.P., *Massive Transfusion*, Perioperative Transfusion Medicine, p. 351-364 (1998).

Weiskopf, R.B., et al., *Human Cardiovascular and Metabolic Response to Actue, Severe Isovolemic anemia*, JAMA 279(3): 217-221 (Jan. 1998).

Wilkerson, D.K., et al., *Limits of cardiac compensation in anemic baboons*, Surgery, 103(6):665-670 (1988).

Levy, P.S., et al., *Oxygen Extraction Ratio: A Valid Indicator of Transfusion Need in a Limited Coronary Vascular Reserve?* J. Trauma 32(6):769-774 (Jun. 1992).

Schwartz, J.P., et al., *The Influence of Coronary Stenosis On Transfusion Need.*, Cardiothoracic Surgery, Surgical Forum XLIV:226-228 (1993).

Moss, G.S., et al., *Transport of Oxygen and Carbon Dioxide by Hemoglobin-Saline Solution in the Red Cell-Free Primate*, Surg. Gynecol Obstet, 142:357-362 (Mar. 1976).

Frantantoni, J.C., *Points to consider on efficiacy evaluation of hemoglobin and perfluorocarbon based oxygen carriers*, Transfusion 34(8):712-713 (1994).

Frantantoni, J.C., *Red Cell Subsitutes: Evolution of Approaches for Demonstrating Efficacy*, Blood-substitutes—Present and Future Perspectives, Elsevier Science S.A., p. 33-39 (1998).

*Intensive Care. Resuscitation. First Aid*, Malyshev, V.D., Ed., Moscow, "Meditsina", p. 142 (2000) (with translation).

*Clinical Surgery*, Condon, R., et al. Eds, pp. 204-208; pp. 433-434 (1998) (with translation).

\* cited by examiner

METHOD FOR TREATING PATIENTS WITH MASSIVE BLOOD LOSS

RELATED APPLICATION

This application claims the benefit of U.S. Provisional Patent Application Ser. No. 60/415,935, filed Oct. 3, 2002.

BACKGROUND OF THE INVENTION

1. Field of the Invention

The invention relates to the use of hemoglobin solutions to treat patients in need of blood or other oxygen carrier. More specifically, the invention relates to the administration of a hemoglobin solution to patients suffering from massive blood loss.

2. Description of the Related Art

The following description refers to a number of references by numeral in parentheses. Complete citations to the references may be found in the section entitled "References" immediately preceding the claims.

The critical issues in resuscitation from acute blood loss in trauma and surgery are restoration of total blood volume and maintenance of sufficient oxygen-carrying capacity to avoid inadequate delivery of oxygen to tissues. (1, 2, 3, 4) Inadequate volume replacement leads to a fall in blood pressure and eventual hypovolemic shock. Insufficient red cell replacement may lead to critical levels of anemia, irreversible ischemia, and death. (5, 6)

The physiologic consequences of profound anemia are well understood. In a bleeding but otherwise healthy surgical patient, cardiovascular compensation should be adequate until red blood cell (RBC) hemoglobin concentration falls below of 5 g/dL. (26) As blood loss continues and the RBC hemoglobin concentration falls further, the compensatory responses begin to fail. (7, 8, 29, 31) Cardiac compensation becomes inadequate when RBC hemoglobin concentration falls below 3.5 g/dL, (32, 33, 34, 35) with reported mortality rates ranging from 50-95% when the RBC hemoglobin concentration falls below 3 g/dL. (9, 10, 11, 12, 13, 14, 29)

Current resuscitation methods involve initial asanguineous (non-blood) volume replacement with salt solutions, followed by red cell transfusions when compatible blood is available and adequate in supply. (1, 2) The goal of current treatment methods is to restore sufficient blood volume to maintain a mean arterial pressure above 60 mmHg, and to replace sufficient red cells to maintain a circulating hemoglobin level above 6 g/dL according to the American Society of Anesthesiologists (ASA), (7) or between 7-10 g/dL according to the National Institutes of Health (NIH) Consensus Conference. (8) However, there are occasions when red cells are temporarily unavailable, inadequate in supply, or cannot be used due to incompatibility or religious objection. This may lead to urgent, life-threatening situations, with reported mortality rates of 50-95% for hemoglobin levels $\leq 3$ g/dL. (9, 10, 1, 12, 13, 14) What is needed in these situations is a substitute for whole blood such as a solution for restoring volume as well as oxygen carrying capacity. Moreover, considering the risks of infection or other toxicity associated with blood replacement therapy, patients may choose an oxygen carrier solution to restore volume and oxygen carrying capacity, even when whole blood is available.

Prior to the present invention, the benefits of using a polymerized hemoglobin solution as a treatment for massively bleeding patients had not been studied. While U.S. Pat. No. 6,498,141 teaches that up to 5 L of a hemoglobin solution may be administered to a patient, there has been no suggestion of the use of a polymerized hemoglobin solution to treat patients suffering from massive hemorrhage, including those patients having total Hb less than 7 g/dL. It had been reported that nearly all patients with Hb level less than 5 g/dL, who decline blood transfusion, die without the use of extreme measures such as hypotensive anesthesia, hypothermia, muscle paralysis and sedation. (29) However, despite the need for a non-blood therapy to treat massive hemorrhage, the use of a substitute for blood, such as an oxygen carrying polymerized hemoglobin solution, has not been addressed for such treatment.

What is needed is an alternative oxygen-carrier that can be administered in large quantities and provide immediate life-sustaining therapy until adequate red blood cell hemoglobin levels (RBC hemoglobin concentration) can be restored.

SUMMARY OF THE INVENTION

In on aspect, the invention provides a method for treating a mammal suffering from a life threatening level of red blood cell hemoglobin (RBC Hb) as the result of blood loss. The method includes administering to the mammal a polymerized hemoglobin solution.

In another aspect, the invention provides a method of preventing anemia, irreversible ischemia, or hypovolemic shock in a patient suffering from massive blood loss. The method includes administering to the patient a volume of a polymerized hemoglobin solution sufficient to maintain total Hb above 5.0 g/l and arterial pressure above 60 mmHg.

In a further aspect, the invention provides a method of maintaining mean circulating Hb levels above 5.0 g/dL in a patient suffering from massive blood loss. The method includes administering to the patient a polymerized hemoglobin solution in an amount of at least one blood volume of the patient.

Still further, the invention provides a method for treating a human having a hemoglobin concentration below about 7 g/dL as the result of a massive blood loss. The method includes administering to the human a polymerized hemoglobin solution.

In yet another aspect, the invention provides a method for sustaining life in a human suffering from massive blood loss. The method includes preventing hypovolemic shock and further decrease in blood pressure by administering to the human a polymerized hemoglobin solution.

In the various aspects of the invention, the hemoglobin solution may be an acellular solution comprising an essentially tetramer-free, cross-linked, polymerized hemoglobin solution which is substantially free of stroma and other contaminants. The hemoglobin solution may be administered in an amount of at least 5 L or at least one blood volume of the patient. The administration of the hemoglobin solution may maintain a mean circulating hemoglobin level greater than 5.0 g/dL and arterial pressure above 60 mmHg. The hemoglobin solution may be administered at a rate of at least 2 units per minute and may avoid the toxicities associated with vasoconstriction, and renal, pancreatic, gastrointestinal and cardiac dysfunction.

In addition, the polymerized hemoglobin may have a molecular weight distribution of:

(a) from about 5-30% by weight of polymerized hemoglobin of polymer having a molecular weight of about 128 KDa;

(b) from about 15-35% by weight of polymerized hemoglobin of polymer having a molecular weight of about 192 KDa; and (c) from about 35-75% by weight of polymerized hemoglobin of polymer having a molecular weight of about 256 KDa.

BRIEF DESCRIPTION OF THE FIGURES

Specific embodiments of the invention are described with reference to the following drawings, wherein.

DETAILED DESCRIPTION

Figure 1:
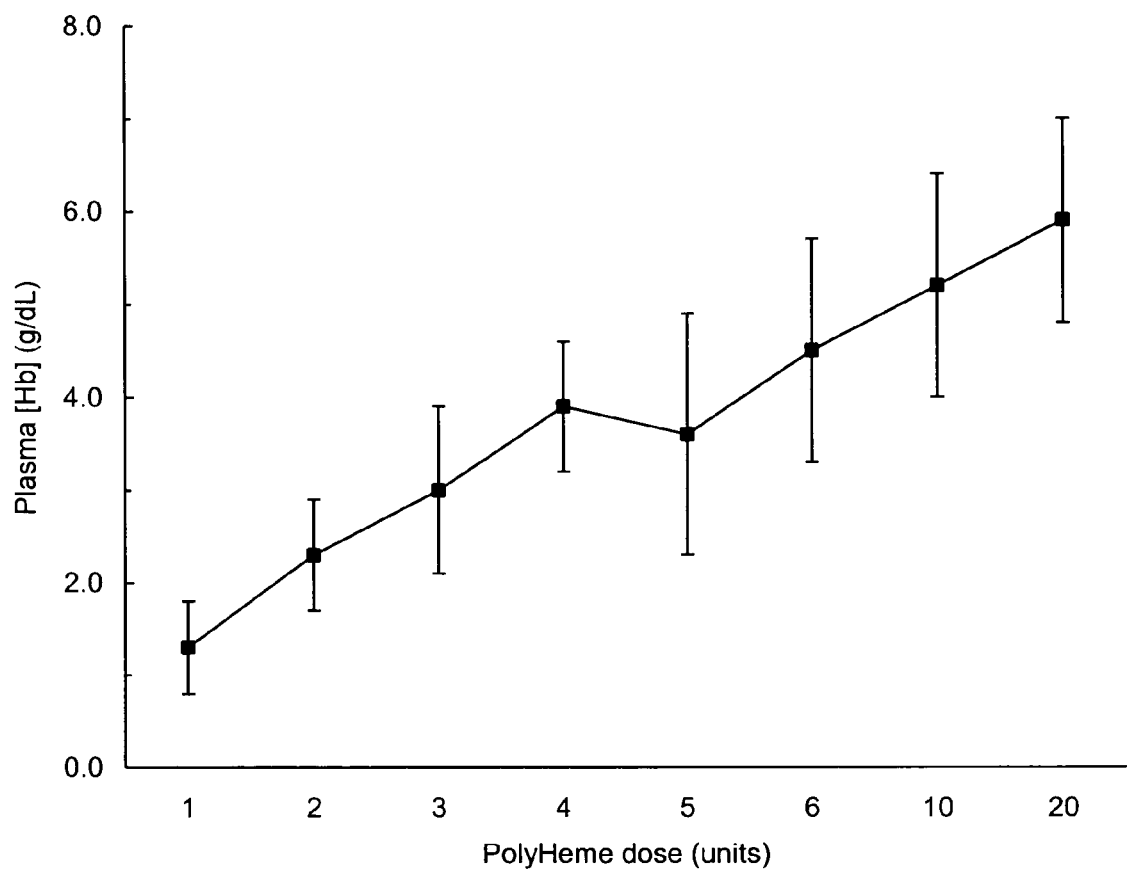
FIG. 1 is a graph depicting the mean (±SD) plasma hemoglobin concentration versus dose of polymerized hemoglobin solution. One unit of the polymerized hemoglobin solution contains 50 g polymerized hemoglobin in 0.5 L.

Before describing the present invention in further detail, a number of terms will be defined. As used herein, the singular forms "a," "an," and "the" include plural referents unless the context clearly dictates otherwise.

As used herein, the term "cross-linked" means the chemical emplacement of molecular "bridges" onto or into a molecule, or between molecules with the purpose of altering the shape, size, function or physical characteristics of the molecule. Cross-linked molecules may be polymerized or non-polymerized, i.e., cross-linked molecules may be tetrameric.

As used herein, the term "tetramer" refers to hemoglobin molecules having a molecular weight of about 64 KDa; that is, the term refers to both native and intramolecularly crosslinked hemoglobin molecules.

As used herein, the term "essentially tetramer free" denotes the level of purity with respect to tetramer contamination at which certain biological responses to tetramer administered into a mammal are no longer present. A main criterion is the absence of alterations in renal function when pharmaceutically effective amounts are infused, that is, at a level of purity of about 99% or better (less than about 1% of tetramer is present). The preferred product produced by the inventive process contains no more than about 0.8% tetramer based on the weight of total hemoglobin (THb). In other words, an essentially tetramer-free product according to the invention contains no more then physiologically acceptable amounts of unpolymerized hemoglobin tetramer. Particularly preferred products of the invention contain less than about 0.5% tetramer; the most particularly preferred products of the invention contain about 0.3-0.4% tetramer. Such amounts of tetramer have been found to be physiologically acceptable.

As used herein, the terms "ultrapurified product" or "purified product" have the same meaning as the term "essentially tetramer-free."

As used herein, % total hemoglobin (THb) is defined as grams of hemoglobin/100 mL of solution.

As used herein, the term "polymerizing solution" means a solution containing a "cross-linking" or polymerizing agent, such as glutaraldehyde, imido esters, diaspirin or others, in a biochemically suitable carrier.

As used herein, the term polymerized means the placement of molecular bridges between molecules or tetrameric subunits where the size and weight of the resulting polymerized molecule is increased with respect to native or tetrameric hemoglobin. Polymerized hemoglobin is not tetrameric hemoglobin.

Patients suffering from massive blood loss are in immediate need of blood or an alternative oxygen carrier. It has been found that polymerized hemoglobin solutions can be used to treat such patients in lieu of providing asanguineous solutions followed by RBCs infusion. In the method of the invention, it has been discovered that up to at least twenty units (10 L), or about two blood volumes of a patient, with a polymerized hemoglobin solution can be administered to massively bleeding patients, in lieu of red cells, as their initial oxygen-carrying replacement. The method can sustain life during rapid, massive hemorrhage in patients with life-threatening RBC hemoglobin concentration levels who do not receive red cells. Alternatively, polymerized hemoglobin may be administered according to the invention in combination with red blood cells. The administration of polymerized hemoglobin can be at approximately the same time, or substantially before or after the administration of red blood cells.

In order to be useful for treating patients with massive blood loss, the polymerized hemoglobin solution is preferably an oxygen-carrying resuscitative fluid, universally compatible, immediately available, and disease-free. The solution is preferably capable of being infused rapidly and in massive quantities, and the solution must avoid the toxicities observed historically with unmodified hemoglobin (16, 17, 18, 19) and in recent trials with modified hemoglobins (20, 21, 22, 23). These toxicities include vasoconstriction and renal, pancreatic, gastrointestinal, and cardiac dysfunction. The small molecular-weight tetrameric species of hemoglobin have been associated with these unacceptable adverse effects.

In one aspect of the invention, the polymerized hemoglobin solution has the following general characteristics shown in Table 1.

TABLE 1

| | |
|---|---|
| Total Hemoglobin (g/dl)[1] | 9.5-12.0 |
| Methemoglobin (% of total Hb)[1] | <8.0 |
| Carboxyhemoglobin (% of total Hb)[1] | <5.0 |
| $P_{50}$ (torr)[1] | 23-32 |
| Osmolality (mmol/Kg)[2] | 280-360 |
| Sodium (mmol/L)[3] | 135-155 |
| Potassium (mmol/L)[3] | 3.5-4.5 |
| Chloride (mmol/L)[3] | 85-110 |
| Free Iron (ppm)[4] | <2.0 |

TABLE 1-continued

| | |
|---|---|
| Molecular Wt. Dist. – 128 KDa peak (%)[5] | 5-30 |
| Molecular Wt. Dist. – 192 KDa peak (%)[5] | 15-35 |
| Molecular Wt. Dist. – 256 KDa peak (%)[5] | 35-75 |
| Tetramer (64K)(%)[5] | <1.0 |
| Phospholipids ng/Hb[6] | <50 |
| Glycolipids (ng/Hb)[6] | <2 |

[1]determined spectrophotometrically.
[2]determined by osmometry.
[3]determined by ion specific electrode.
[4]determined by atomic aborption.
[5]Determined by size exclusion-HPLC, % by weight of polymerized hemoglobin.
[6]Determined by HPTLC One example of a hemoglobin solution useful in the invention is POLYHEME® acellular red blood cell substitute (Northfield Laboratories, Inc., Evanston, Ill.). POLYHEME® acellular red blood cell substitute is a sterile, pyrogen-free, isotonic, and isooncotic hemoglobin solution. The solution loads and unloads oxygen similarly to red cells, the basic requirement for any oxygen carrier. (15, 24, 36, 37). Some properties of a unit of this hemoglobin solution are summarized in Table 2

TABLE 2

Characteristics of POLYHEME® acellular red blood cell substitute

| Index (per unit) | Measurement |
|---|---|
| Volume | 500 mL |
| Mass Hemoglobin | 50 g |
| Concentration Hb | 10 g/dL |
| $P_{50}$ | 26-32 mm Hg |
| Concentration MetHb (w/w) | <8.0% |
| Concentration Tetramer (w/w) | ≦1.0% |
| half life ($t_{1/2}$) | 24 hours |
| Shelf-life | >1 year |

$P_{50}$ = oxygen tension at 50% hemoglobin saturation

The preparation of POLYHEME® acellular red blood cell substitute is designed to avoid the toxicities commonly associated with hemoglobin solution, and involves polymerization with glutaraldehyde and subsequent purification to remove all unpolymerized tetramer. Early experience demonstrated that infusion to six units of POLYHEME® acellular red blood cell substitute in urgent blood loss was well tolerated, and avoided the toxicities associate with hemoglobin solutions. (24, 25) Preparation of suitable hemoglobin solutions, such as POLYHEME® acellular red blood cell substitute, can be prepared as shown in Example 8.

One unit of POLYHEME® acellular red blood cell substitute is a solution containing 50 g of hemoglobin in 500 mL (10 g/dL). This is equivalent to the mass of hemoglobin functionally delivered in a 1-unit red cell transfusion. POLYHEME® acellular red blood cell substitute has a shelf-life of greater than one year at 2-8° C.

Other hemoglobin solutions are known to those in the art including hemoglobin solutions derived from non-human blood. These solutions may be useful for the method of the present invention provided they are capable of being infused rapidly and in massive quantities, and the solutions avoid the toxicities commonly associated with hemoglobin solutions. In addition, such solutions should load and unload oxygen similar to red cells.

Patients suffering from life threatening massive blood loss are generally recognized as those patients having lost at least about sixty percent of one blood volume, or typically about one full blood volume (one full blood volume is about 5 L in a 70 kg man). The volume will vary depending upon the size and other factors. Blood loss of this quantity is typically the result of trauma, hemorrhage or surgery. Patients suffering from massive blood loss may receive a hemoglobin solution in lieu of red cells as an initial oxygen-carrying replacement. Rapid administration of the hemoglobin solution may be accomplished by methods readily employed for infusion/transfusion therapy. It has been found that patients suffering massive blood loss tolerate polymerized hemoglobin infusion at rates of two units or more per minute.

Where red cells are temporarily unavailable or cannot be used, infusion of a hemoglobin solution, such as POLYHEME® acellular red blood cell substitute, has been shown to improve survival in patients having RBC hemoglobin concentrations below about 5 g/dL prior to infusion. In various embodiments of the invention, a patient may receive up to 20 units of a hemoglobin solution, such as PolyHeme™. Since the average blood volume in a normal human is approximately 10 units or 5 liters, this represents a massive transfusion of about a two total blood volume exchange.

Figure 3:
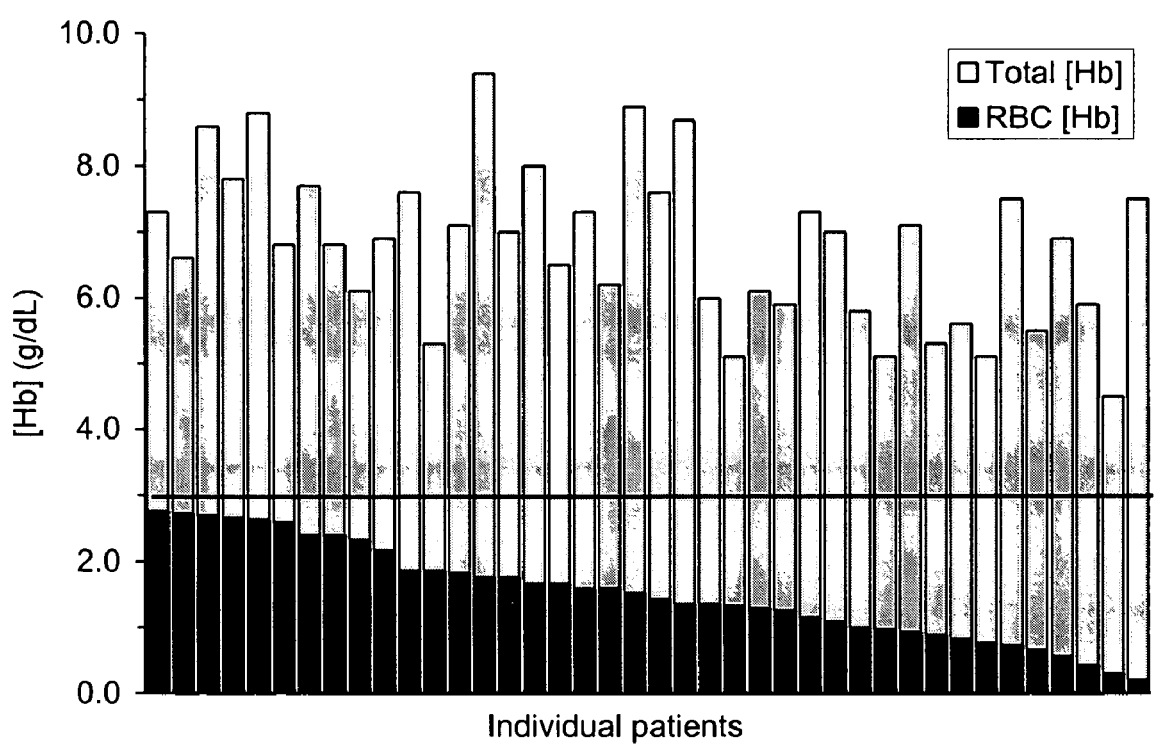
FIG. 3 is graph depicting individual patient data for 40 patients with nadir RBC hemoglobin solution ≦3 g/dL, showing the total hemoglobin concentration as the sum of RBC hemoglobin concentration and plasma hemoglobin concentration. The line represents life-threatening level of 3 g/dL.

According to the present invention, infusion of a polymerized hemoglobin solution maintains the total hemoglobin concentration in therapeutically adequate range (>5.0 g/dL) even though patients have RBC hemoglobin concentration levels ≦3 g/dL. FIG. 3 shows the substantial hemoglobin concentration reserve provided by POLYHEME® acellular red blood cell substitute in each of various individuals at such critically low RBC hemoglobin concentration levels.

Figure 4:
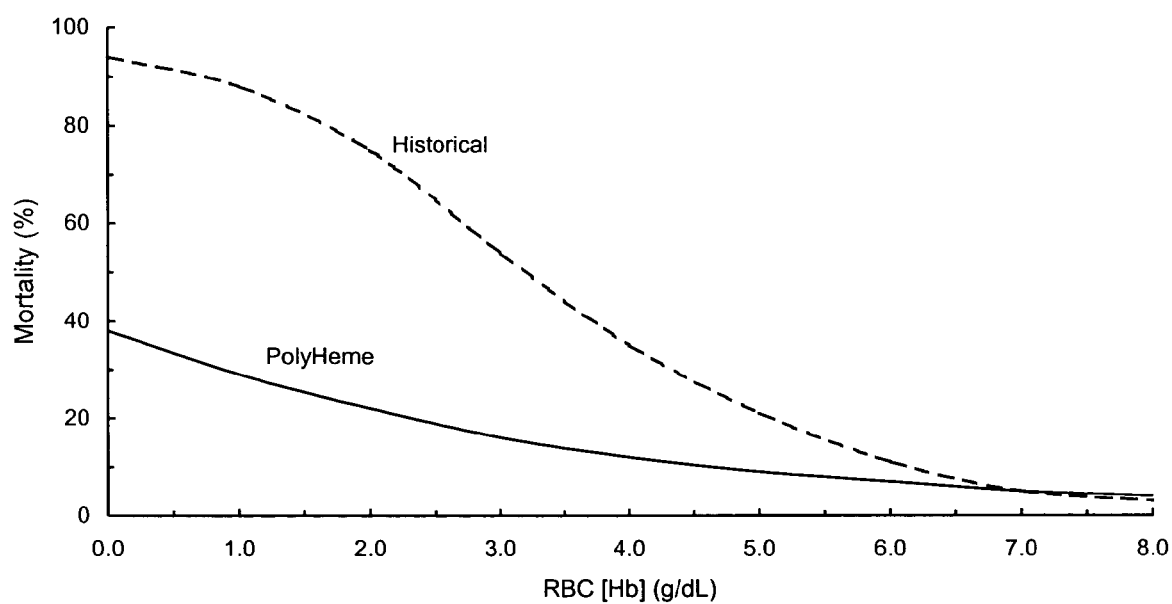
FIG. 4 is a logistic regression showing mortality in patients who received POLYHEME® acellular red blood cell substitute and in historical controls. Mortality increases in both groups as RBC hemoglobin concentration falls. Curves begin to separate at RBC hemoglobin concentration of about 7.0 g/dL and become significantly different ($p<0.05$) at RBC hemoglobin concentration below about 5.0 g/dL.

FIG. 4 shows a comparison of the mortality of patients receiving no treatment and patients receiving POLYHEME® acellular red blood cell substitute. Although mortality increases as RBC hemoglobin concentration falls in both groups, the curves begin to separate as hemoglobin concentration falls below about 7 g/dL and become significantly different below hemoglobin concentration of 5 g/dL where the mortality rate is improved for patients receiving POLYHEME® acellular red blood cell substitute. This observation is consistent with the physiologic observations documenting adequate cardiovascular compensation to hemoglobin concentration of 5 g/dL. (26)

Hemoglobin solutions can simplify and facilitate the early treatment of urgent blood loss by permitting immediate, rapid, and simultaneous volume expansion and hemoglobin replacement without red cell transfusion. Such solutions have the ability to avoid the onset of life-threatening anemia and subsequent mortality until critical bleeding can be surgically controlled and red cell transfusions are available. The use of hemoglobin solutions to provide life-sustaining therapy by maintaining adequate total hemoglobin concentration during urgent hemorrhage is appropriate, even if the follow-up period requires subsequent transfusion with red cells. Additional benefits of the use of hemoglobin solutions over RBCs are prolonged storage capability, safety during administration, and the avoidance of clerical errors during such ongoing massive hemorrhage.

EXAMPLES

Example 1

Study Populations 30-day mortality in patients receiving POLYHEME® acellular red blood cell substitute was compared to a historical control group of patients who declined blood transfusion for religious reasons. Male and female patients at least 18 years of age were eligible based on the following inclusion criteria: urgent blood loss due to trauma and/or surgery, clinical decision for urgent transfusion in anticipation of low hemoglobin concentration, and/or systolic blood pressure <100 mmHg due to blood loss. The exclusion criteria included: severe head trauma (Glasgow Coma Scale score ≦8), lack of acute blood loss, signs or symptoms of severe organ dysfunction, or pregnancy. The study was conducted at American College of Surgeons certified Level I trauma centers and tertiary care referral institutions.

There are numerous reports in the literature describing the pooled outcome in bleeding patients who refuse blood due to religious objection. A single study was chosen as the basis for comparison because the data are from a single investigator and, thus, the methodology used in collection and analysis of the data are standardized. (29) In addition to being the largest series of patients (n=300) with hemoglobin concentration ≦8 g/dL, the actual individual patient hemoglobin concentration measurements are used, unlike the pooled classification in other reports. The common demographic and medical characteristics in the treatment and historical control groups were age, ASA physical status score, cardiovascular risk or history, date of admission, gender, race, and hospital site. Although the two groups differed on all of these parameters, supportive modeling determined that none of these parameters altered the outcome of the original analysis. The important similarity is the progressive blood loss in the surgical setting unaccompanied by red cell replacement. While there have been advances in critical care in recent years, there remains a high mortality associated with progressive anemia, particularly hemoglobin concentration levels ≦3 g/dL.

Example 2

Methods

All POLYHEME® acellular red blood cell substitute patients received the same treatment following the Advanced Trauma Life Support and American Association of Blood Banks guidelines on fluid and transfusion therapy, except that POLYHEME® acellular red blood cell substitute was infused in lieu of red cells when a clinical decision was made that transfusion of oxygen-carrying therapy was indicated. All patients received infusions of 1-2 liters of crystalloid as their initial volume replacement. The indication for and rate of infusion of POLYHEME® acellular red blood cell substitute depended upon the patient's clinical status. Patients were eligible to receive up to 1, 3, 6, 10, and finally 20 units of POLYHEME® acellular red blood cell substitute as the allowable dose escalated. If patients required additional oxygen-carrying therapy after the maximum dose of POLYHEME® acellular red blood cell substitute was reached, red cells were transfused as indicated. Clotting factors and platelets were administered when indicated following high volume blood loss. POLYHEME® acellular red blood cell substitute was infused preoperatively, intraoperatively, and postoperatively to awake and anesthetized patients in emergency rooms, operating rooms, and intensive care units.

Example 3

Hemoglobin Determinations

As shown in the equation below, following infusion of POLYHEME® acellular red blood cell substitute, the total hemoglobin is equal to the sum of the hemoglobin carried by the red cells and by the POLYHEME® acellular red blood cell substitute in the plasma.

Total hemoglobin concentration=RBC hemoglobin concentration+Poly hemoglobin concentration The plasma and red cells were separated to quantify the hemoglobin carried by each component. Total hemoglobin concentration and plasma hemoglobin concentration were determined on whole blood and plasma samples, respectively, using automated cell counters. The RBC hemoglobin concentration was derived from the hematocrit (Hct), measured by the cell counter, as Hct/3. It was therefore possible to document the progressive fall in RBC hemoglobin concentration that occurs due to ongoing blood loss not treated with red cell replacement, and observe the impact of the POLYHEME® acellular red blood cell substitute in the plasma in maintaining total hemoglobin concentration.

Example 4

Statistical Analysis

The mean and standard deviation are reported for continuous variables, and the frequency and percent are reported for nominal variables.

Logistic regression was used to analyze mortality. Terms for treatment group (POLYHEME® acellular red blood cell substitute or historical control), nadir RBC hemoglobin concentration, and their interaction were used. The interaction between RBC hemoglobin concentration and treatment group is considered appropriate for analysis of mortality because at sufficiently high hemoglobin concentration the patient will not be at risk of death due to anemia, and as hemoglobin concentration decreases the risk of death is expected to increase. Patients whose RBC hemoglobin concentration was >8 g/dL were not included as they were not at risk of death due to anemia.

A supportive analysis was run to test if any differences observed could be due to demographic/medical characteristic parameters. The parameters available in the treatment and historical control groups were age, ASA physical status score, cardiovascular risk, gender, hospital, race, and year of operation. Each of these parameters with their interaction with RBC hemoglobin concentration and treatment was tested separately in preliminary models. Subsequently, all significant demographic parameters were included in a full logistic regression analysis.

Example 5

Results

The 171 patients ranged in age between 17 and 85 years. The etiology of blood loss in these patients included blunt trauma (n=86), penetrating trauma (n=41), and non-traumatic origin (n=44). The dose of POLYHEME® acellular red blood cell substitute received by the 171 patients is shown in Table 3. The maximum rate of infusion was approximately 2 units per minute in uncontrolled hemorrhage.

TABLE 3

Dose of POLYHEME ®
acellular red blood cell substitute Infused

| Units | Mass (g) | Volume (L) | Recipients |
|---|---|---|---|
| 1-2 | 50-100 | 0.5-1.0 | 45 |
| 3-4 | 150-200 | 1.5-2.0 | 45 |
| 5-9 | 250-450 | 2.5-4.5 | 47 |
| 10-20 | 500-1000 | 5.0-10.0 | 34 |

Figure 2:
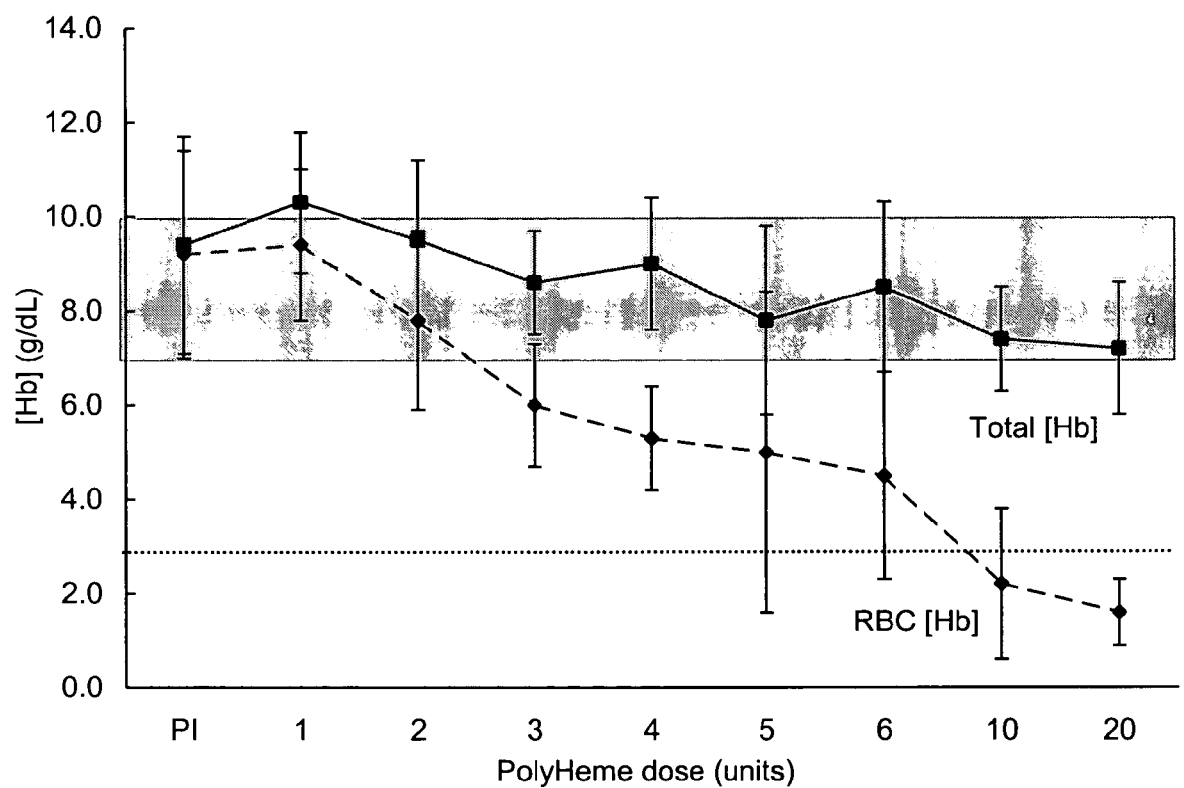
FIG. 2 is a graph depicting the mean (±SD) total hemoglobin concentration (solid line) and RBC hemoglobin concentration (dashed line) versus dose of a polymerized hemoglobin solution. The shaded area represents 7-10 g/dL guideline according to NIH Consensus Statement. The dotted line represents life threatening level of 3 g/dL. One unit of the polymerized hemoglobin solution contains 50 g of polymerized hemoglobin in 0.5 L.

The hemoglobin relationships are demonstrated in FIGS. 1, 2, and 3. The increase in plasma hemoglobin concentration with increasing doses of POLYHEME® acellular red blood cell substitute is shown in FIG. 1. The maximum plasma hemoglobin concentration was 8.0 g/dL in a single patient who received 8 units of POLYHEMEO acellular red blood cell substitute. The maximum mean plasma hemoglobin concentration was 5.9±1.1 g/dL in the group of patients who received 20 units of POLYHEME® acellular red blood cell substitute, reflecting the equilibrium between ongoing blood loss and replacement.

The relationship between total hemoglobin concentration and RBC hemoglobin concentration for all patients is shown in FIG. 2. The figure illustrates that as RBC hemoglobin concentration falls due to progressive hemorrhage without red cell transfusion, total hemoglobin concentration is maintained in the 7-10 g/dL range by the infusion of POLYHEME® acellular red blood cell substitute. With hemorrhage requiring more than six units of POLYHEME® acellular red blood cell substitute, the RBC hemoglobin concentration falls below the life-threatening level of 3 g/dL.

There were 40 patients who had a RBC hemoglobin concentration $\leq 3$ g/dL. FIG. 3 shows the total hemoglobin concentration for each individual patient as the sum of RBC hemoglobin concentration and plasma hemoglobin concentration. The patient on the far right had a RBC hemoglobin concentration of 0.2 g/dL, with a total hemoglobin concentration of 7.5 g/dL. Twenty-nine patients had total hemoglobin concentration $\geq 6$ g/dL. Of the 11 patients with total hemoglobin concentration <6 g/dL, only two patients received the full 20 unit dose. All patients had total hemoglobin concentration considerably greater than the critical 3 g/dL level.

The mortality data are shown in Table 4. There were 18 deaths overall out of 171 patients for a mortality of 10.5%. Although mortality increased as RBC hemoglobin concentration fell, there was no further increase as the RBC hemoglobin concentration fell below 3 g/dL. Nine of the 12 patients with RBC hemoglobin concentration $\leq 1$ g/dL survived.

TABLE 4

Cumulative Mortality by Nadir Post-Infusion RBC
Hemoglobin Level in POLYHEME ® acellular red blood
cell substitute Recipients (N = 171)

| RBC hemoglobin concentration (g/dL) | Deaths/Patients | Mortality (%) | 95% CI (%) |
|---|---|---|---|
| $\leq 12.0$ | 18/171 | 10.5 | 6.4 to 16.1 |
| $\leq 11.0$ | 18/170 | 10.6 | 6.4 to 16.4 |
| $\leq 10.0$ | 18/165 | 10.9 | 6.6 to 16.7 |
| $\leq 9.0$ | 18/158 | 11.4 | 6.9 to 17.4 |
| $\leq 8.0$ | 16/150 | 10.7 | 6.2 to 16.8 |
| $\leq 7.0$ | 15/133 | 11.3 | 6.5 to 17.9 |

TABLE 4-continued

Cumulative Mortality by Nadir Post-Infusion RBC
Hemoglobin Level in POLYHEME ® acellular red blood
cell substitute Recipients (N = 171)

| RBC hemoglobin concentration (g/dL) | Deaths/Patients | Mortality (%) | 95% CI (%) |
|---|---|---|---|
| $\leq 6.0$ | 14/100 | 14.0 | 7.8 to 22.2 |
| $\leq 5.0$ | 14/84 | 16.7 | 9.3 to 26.1 |
| $\leq 4.0$ | 13/62 | 21.0 | 11.5 to 32.7 |
| $\leq 3.0$ | 10/40 | 25.0 | 12.7 to 41.2 |
| $\leq 2.0$ | 8/30 | 26.7 | 12.3 to 45.9 |
| $\leq 1.0$ | 3/12 | 25.0 | 5.5 to 57.2 |

CI = confidence interval.

Ten deaths occurred at an early stage (Day 0-Day 1), all due to exsanguination, including one that was the result of an unknown pre-existing liver disease which compromised hemostasis. Three deaths occurred at an intermediate stage (Day 1-Day 7). One was due to exsanguination, and the other two were due to the presenting injury. Five deaths occurred at a late stage (Day 7 or later). Four were due to multiple organ failure, and one was due to complications from pre-existing pulmonary fibrosis. None of the deaths was considered due to POLYHEME® acellular red blood cell substitute.

Example 6

Historical Controls

Table 5 shows the mortality data for the 300 historical control patients. There were 48 deaths overall for a mortality of 16.0%. There is a marked increase in mortality as RBC hemoglobin concentration falls, with no survivors at RBC hemoglobin concentration $\leq 2$ g/dL.

TABLE 5

Cumulative Mortality by Nadir Post-Infusion
RBC Hemoglobin Level in Historical Controls (N = 300)

| RBC Hemoglobin Concentration (g/dL) | Deaths/Patients | Mortality (%) | 95% CI (%) |
|---|---|---|---|
| $\leq 8.0$ | 48/300 | 16.0 | 12.0 to 20.6 |
| $\leq 7.0$ | 48/201 | 23.9 | 18.2 to 30.4 |
| $\leq 6.0$ | 43/145 | 29.7 | 22.4 to 37.8 |
| $\leq 5.0$ | 38/91 | 41.8 | 31.5 to 52.6 |
| $\leq 4.0$ | 27/59 | 45.8 | 32.7 to 59.3 |
| $\leq 3.0$ | 20/31 | 64.5 | 45.4 to 80.8 |
| $\leq 2.0$ | 7/7 | 100.0 | 59.0 to 100.0 |
| $\leq 1.0$ | — | — | — |

Example 7

Mortality Comparison

The logistic regression produced two different curves (FIG. 4), one for each treatment group. Although mortality increased in both groups as RBC hemoglobin concentration decreased, the mortality in the POLYHEME® acellular red blood cell substitute group was lower than the historical controls at all RBC hemoglobin concentration levels below 7.3 g/dL. This reduction reached significance at all RBC hemoglobin concentration levels below 5.3 g/dL (p<0.05).

The two groups differed on the following demographic and medical characteristics: age, ASA physical status score, treatment group, nadir RBC hemoglobin concentration, and their interaction ($p<0.05$). However, supportive modeling determined that none of these parameters altered the outcome of the original analysis.

Example 8

Preparation of Hemoglobin Solutions

POLYHEME® acellular red blood cell substitute can be prepared by the following methods. Various modifications to the process are described in U.S. Pat. No. 6,498,141, the disclosure of which is incorporated herein by reference in its entirety.

1. Cell Aspiration and Filtration

Donor bags of outdated blood are punctured and about 150 ml of a 1% (w/v) aqueous sodium chloride solution is introduced into the bag. The bags are aspirated under reduced pressure or vacuum. The aspirated blood is passed through three leukocyte adsorption depth filters. Typically, about 225 units of outdated whole blood are aspirated, filtered and subsequently transferred to Tank 1. The filters are then rinsed with about 75 liters of a 1% (w/v) aqueous sodium chloride solution.

2. Cell Wash and Lysis

Prior to the introduction of the blood into Tank 1, Tank 1 is charged with about 40-50 L of a 1% aqueous sodium chloride solution. After all 225 units of outdated whole blood have been aspirated, filtered and transferred, and the filters have been rinsed, the tank and associated piping contains about 365-390 liters of a 4% total hemoglobin solution. During the aspiration and filtering steps, Tank 1 is maintained at a reduced pressure, i.e., a vacuum of 20-28" Hg. Once all the outdated blood has been transferred to Tank 1, the vacuum is switched off and carbon monoxide is introduced into the tank so that the tank contains an atmosphere of carbon monoxide.

Tank 1 is coupled to a 0.65μ tangential flow filter. The initial charge of 365-390 liters of 4% total hemoglobin solution is concentrated to approximately 215-225 L of an 7% total hemoglobin solution by microfiltration through the tangential flow filter. The pH of the hemoglobin solution at this point is about 6 to 6.5. Subsequent to concentrating to 7% total hemoglobin, the solution is washed by adding a 1% (w/v) sodium chloride solution, diafiltering and removing the filtrate at the same rate sodium chloride solution is added. The 215-225 L of hemoglobin solution is typically washed with about 8 volumes of the 1% sodium chloride solution (about 1,800 L). Subsequent to washing, the solution is concentrated to about 90-95 L, i.e., about 16% total hemoglobin, and "water for injection" (WFI) is added to bring the volume of the solution up to about 220 L. With the addition of the WFI, the cells swell and rupture releasing hemoglobin into solution. The concentration of the resulting hemoglobin solution is about 7% total hemoglobin (THb).

The resulting solution is clarified while still in Tank 1. The solution is first concentrated to about 90 L and the filtrate transferred to Tank 2. As the solution is pumped across the filter, red blood cells stroma contaminants and cell wall material is retained and removed by the filter. The remaining 90 L of solution in Tank 1 is washed (diafiltered) with about 280 L of WFI. This volume of wash is added to Tank 2. The volume resulting in Tank 2 is about 405-415 L of a 3.3% total hemoglobin solution.

3. Heat Treatment

The resulting solution of stroma-free hemoglobin is then heat treated in Tank 2 at a temperature of about 60-62° C. over a period of about 10 hours. During this time, the solution is moderately agitated. As the solution is heated and passes a temperature of about 55° C., a precipitate forms.

4. Clarification and Viral Reduction

The resulting 3.3% THb (w/v) stroma-free, heat treated hemoglobin solution is then filtered through a 0.2μ pre-filter followed by a 0.1μ pre-filter and then pumped through a 100 kDa viral reduction ultrafilter into Tank 3.

5. UltraFiltration Concentration

The filtered hemoglobin solution is then concentrated to 85-105 liters (about 14% THb) and subsequently washed and diafiltered with 4 volumes of WFI (350 L). The concentration and diafiltration is accomplished using a 10 kilodalton (kDa) molecular weight ultrafilter. A drain associated with ultrafilter collects filtrate. At this point, the hemoglobin solution contains less than 50 ng of phospholipid per gram of hemoglobin and less than 2 ng of glycolipid per gram of hemoglobin (as measured by TLC), less than 1% methemoglobin (as measured by co-oximetry), less than about 0.03 endotoxin units of endotoxin per milliliter at a pH of about 6 to 6.5. This hemoglobin in the solution is primarily carboxyhemoglobin.

6. Degassification

The resulting carboxyhemoglobin solution is then transferred to a 175 L vessel (Tank 4). Oxygen is sparged through the solution at a 66 L/min for 18 hours at 10° C. The resulting solution contains less than 5% carboxyhemoglobin based on the weight of total hemoglobin.

After oxygenation, the solution is sparged with a similar flow of nitrogen for about 3 to 3.5 hours at 10° C. until less than 10% oxyhemoglobin based on the weight of total hemoglobin remains in the solution.

7. Chemical Modification

The deoxyhemoglobin solution is transferred to Tank 5 for chemical modification.

To Tank 5 containing the deoxyhemoglobin at about 4° C. solution is then added an aqueous solution of pyridoxyl-5-phosphate (P5P) (93.75 g/L) at a 1:1 to 3:1 P5P to hemoglobin molar ratio. A 2:1 molar ratio of P5P to hemoglobin is preferred. The pyridoxylation is conducted at a temperature of about 4° C. The P5P solution is typically added over about 1 minute and mixed for approximately 15 minutes, after which a sodium borohydride/sodium hydroxide solution is added to the hemoglobin solution at a molar ratio of sodium borohydride to hemoglobin of about 20:1. A suitable aqueous sodium borohydride/sodium hydroxide solution contains 0.8 g of sodium hydroxide per 2 liters and 90.8 g of sodium borohydride per 2 liters. The borohydride solution is added as rapidly as possible over a period of about 1 minute and then stirred for one hour.

8. Reactant Removal

The resulting 150 L solution of pyridoxylated hemoglobin is subsequently diafiltered using 10K Dalton ultrafilter to remove excess reactants with 4 volumes (600 L) of WFI. A drain associated with the ultrafilter collects the filtrate from the filter.

9. UP Poly Concentration

To Tank 5 containing the pyridoxylated hemoglobin is added sufficient WFI to prepare a 4.5% total hemoglobin solution (about 265 L of hemoglobin solution). A glutaraldehyde solution is added to the pyridoxylated hemoglobin solution at a molar ratio of glutaraldehyde to hemoglobin of about 24:1. The glutaraldehyde solution is typically added over a period of about 2.5 hours by metering pump to the hemoglobin solution. The polymerization reaction is allowed to proceed for about 15-18 hours. The target molecular weight distribution is about 75% polymer and 25% tetramer. The target polymers have molecular weights of less than about 600,000 with a predominant fraction of the molecular weights residing in the 100,000-350,000 range.

When the polymerization reaction reaches the target molecular weight distribution (after about 15-18 hours), aqueous glycine (about 166 g/L) is added (as a quench) to the hemoglobin solution at a 140:1 molar ratio of glycine to hemoglobin. The solution pH at this point is 8.9. The resulting solution is then mixed for about 30-40 minutes after which a sodium borohydride sodium/hydroxide solution (having the concentration identified above) is added to the hemoglobin solution at a 28:1 molar ratio of sodium borohydride to hemoglobin. This resulting mixture is stirred for about 1 hour. The solution is then concentrated to about 150 L by ultrafiltration and washed with 4 volumes (600 L) of WFI. An additional aliquot of sodium borohydride at the same molar ratio as indicated above is added to the concentrated solution and again mixed for 1 hour. The resulting solution is washed with 4 volumes of WFI (600 L) resulting in polymerized, pyridoxylated, stroma-free hemoglobin that has been heat treated.

The resulting solution is oxygenated by allowing the solution to stand under an oxygen atmosphere and is subsequently transferred to a filtration recycle vessel (Tank 10). The hemoglobin is then diluted to about 4% THb. The 4% THb solution is then diafiltered using 10 mM NaCl/20 µM NaOH and a 300,000 molecular weight filter commercially available from Millipore Corp. The filtration is continued until about 97% of the hemoglobin material passes through the filter and into Tank 11 where it is continuously concentrated to 4-8% THb using a 70 kDa ultrafilter. (About 3% of the material, i.e., high molecular weight polymers is retained in Tank 10). The amount of hemoglobin is determined spectrophotometrically using a cooximeter.

The resulting material in Tank 11 is about 4-8% THb and contains about 25% tetramer based on THb. The hemoglobin solution is transferred to Tank 12 and is then diafiltered using 10 mM NaCl/20 µM NaOH buffer and a 100,000 molecular weight filter commercially available from Pall-Filtron. The filtration is continued until the level of tetramer, as determined by size exclusion chromatography using a TOSO BioSep TSKG-3000 SWXL 300×7.8 mm column is less than 1.0. % (typical 0.3%) of the hemoglobin mass by weight. The resulting purified hemoglobin solution remains initially in Tank 11 and is subsequently transferred to gas exchange Tank 8 for deoxygenation.

10. Deoxygenation

Gas exchange Tank 8 is equipped in essentially the same fashion as gas exchange Tank 4. Deoxygenation is accomplished in about 2.5 hours with a nitrogen sparge at about 10° C. and a solution pH of about 8.8. Nitrogen sparging is continued until less than about 16% oxyhemoglobin, based on the weight of total hemoglobin, remains in the solution. The resulting deoxyhemoglobin solution is subsequently transferred to Tank 9 for formulation.

11. Formulation

In formulation Tank 9, the solution is first concentrated to about 7% total hemoglobin. Electrolyte solutions are then added to the hemoglobin solution. Glucose and glycine are added to achieve final concentrations of about 1 g/L and 3.5 g/L respectively. Potassium chloride is added to the solution to obtain a potassium concentration of about 3.5 to 4.5 mM. 3 M sodium chloride is then added to obtain a 85-110 mM chloride concentration. Sodium lactate is subsequently added to obtain a 135-155 mM concentration of sodium ion. A 0.45 molar ascorbic acid solution is added to raise the ascorbic acid concentration up to about 1000 mg/L. Ascorbic acid is added as a preservative/antioxidant for storage. The pH is adjusted to 8.7-9.1@10-15° C. using 0.22 M NaOH. The resulting hemoglobin solution has a final osmolarity of about 280-360 mmole per kg.

The formulated hemoglobin solution is then concentrated to about 10% total hemoglobin using a filter associated with a trap and the 10% hemoglobin solution is then sterilized by filtration and aseptically filled into pre-sterilized bags.

In view of the wide variety of embodiments to which the principles of the present invention can be applied, it should be understood that the illustrated embodiments are exemplary only, and should not be taken as limiting the scope of the present invention. The claims should not be read as limited to the described order or elements unless stated to that effect. Therefore, all embodiments that come within the scope and spirit of the following claims and equivalents thereto are claimed as the invention.

REFERENCES

1. Moore F A, Moore E E. Trauma resuscitation. In: Wilmore D W, Cheung L Y, Harken A H, Holcroft J W, Meakins J L, and Soper N J, editors. ACS Surgery—Principles & Practice. New York: WebMD Corporation Publication; 2002. p. 31-61.
2. American College of Surgeons Committee on Trauma. Advanced Trauma Life Support Program for Physicians 1997 Instructional Manual. 6$^{th}$ ed. Chicago: American College of Surgeons; 1997. p. 97-117.
3. Farion K J, McLellan B A, Boulanger B R, Salazi J P. Changes in red cell transfusion practice among adult trauma victims. *J Trauma* 1998; 44(4):583-587.
4. Baker J B, Korn C S, Robinson K, Chan L, Henderson S O. Type and crossmatch of the trauma patient. *J Trauma* 2001; 50(5):878-881.
5. DeFoe G R, Ross, CS, Olmstead E M, Surgenor S D, Fillinger M P, Groom, R C, et al. Lowest hematocrit on bypass and adverse outcomes associated with coronary artery bypass grafting. *Ann Thorac Surg* 2001; 71:769-776
6. Wu W C, Rathore S S, Wang Y, Radford M J, Krumholz H M. Blood transfusion in elderly patients with acute myocardial infarction. *N Eng J Med* 2001 October 25; 345(17): 1230-1236.
7. Practice guidelines for blood component therapy: A report by the American Society of Anesthesiologists Task Force on Blood Component Therapy. *Anesthesiology* 1996; 84(3):732-747.
8. Consensus Conference. Perioperative red blood cell transfusion. *JAMA* 1988 November; 260(18):2700-2703.
9. Gould S A, Rosen A L, Sehgal L R, Sehgal H L, Langdale L A, Krause, et al. Fluosol DA-20 as a red cell substitute in acute anemia. *N Engl J Med* 1986; 314(26):1653-1656.
10. Spence R K, McCoy S, Costabile J, Norcross E D, Pello M J, Alexander J B, et al. Fluosol DA-20 in the treatment of severe anemia: Randomized, controlled study of 46 patients. *Crit Care Med* 1990; 18(11):1227-1230.
11. Spence R K, Costabile J P, Young G S, Norcross E D, Alexander J B, Pello M J, et al. Is hemoglobin level alone 11. a reliable predictor of outcome in the severely anemic patient? *Am Surg* 1992; 58(2):92-95.
12. Carson J L, Poses R M, Spence R K, Bonavita G Severity of anaemia and operative mortality and morbidity. *Lancet* 1988; 1(8588):727-729.
13. Carson J L, Duff A, Poses R M, Berlin J A, Spence R K, Trout R, et al. Effect of anaemia and cardiovascular disease on surgical mortality and morbidity. *Lancet* 1996; 348(9034):1055-1060.
14. Viele M K, Weiskopf R B. What can we learn about the need for transfusion from patients who refuse blood? The experience with Jehovah's Witnesses. *Transfusion* 1994; 34(5):396-401.
15. Sehgal L R, Gould S A, Rosen A L, Sehgal H L, Moss G S. Polymerized pyridoxylated hemoglobin: a red cell substitute with normal $O_2$ capacity. *Surgery* 1984; 95:433-438.
16. Amberson W R, Jennings J J, Rhode C M. Clinical experience with hemoglobin-saline solutions. *J Appl Physiol* 1949; 1(7):469-489.
17. Brandt J L, Frank N R, Lictman H C. The effects of hemoglobin solutions on renal functions in man. *Blood* 1951; 6:1152-1158.
18. Miller J H, McDonald R K. The effect of hemoglobin on renal function in the human. *J Clin Invest* 1951; 30:1033-1040.
19. Savitsky J P, Docze J, Black J, Arnold J D. A clinical trial of stroma-free hemoglobin. *Clin Pharmacol Ther* 1978; 23(1):73-80.
20. Carmichael F J, Ali A C, Campbell J A, Langlois S F, Willan A R, Pierce C H, et al. A phase I study of oxidized raffinose cross-linked human hemoglobin. *Crit Care Med* 2000 July; 28(7):2283-2292.
21. Kasper S M, Walter M, Grune F, Bischoff A, Erasmi H, and Buzello W. Effects of a hemoglobin-based oxygen carrier (HBOC-201) on hemodynamics and oxygen transport in patients undergoing preoperative hemodilution for elective abdominal aortic surgery. *Anesth Analg* 1996; 83:921-927.
22. LaMuraglia GM, O'Hara P J, Baker W H, Naslund T C, Norris E J, Li J, et al. The reduction of the allogenic transfusion requirement in aortic surgery with a hemoglobin-based solution. *J Vasc Surg* 2000 February; 31(2): 299-308.
23. Sloan E P, Koenigsberg M, Gens D, Cipolle M, Runge J, Mallory M N, et al. Diaspirin cross-linked hemoglobin (DCLHb) in the treatment of severe traumatic hemorrhagic shock. A randomized controlled efficacy trial. *JAMA* 1999; 282:1857-1864.
24. Gould S A, Moore E E, Moore F A, Haenel J B, Burch J M, Sehgal H, et al. Clinical utility of human polymerized hemoglobin as a blood substitute after acute trauma and urgent surgery. *J Trauma* 1997; 43(2):325-332.
25. Gould S A, Moore E E, Hoyt D B, Burch J M, Haenel J B, Garcia J, et al. The first randomized trial of human polymerized hemoglobin as a blood substitute in acute trauma and emergent surgery. *J Am Coll Surg* 1998 August; 187(2): 113-122.
26. Vengelen-Tyler V, editor. American Association of Blood Banks Technical Manual. 13$^{th}$ ed. Bethesda (MD): American Association of Blood Banks; 1999:p. 451-481.
27. Huston P, Peterson R. Withholding proven treatment in clinical research. *N Eng J Med* 2001 September 20; 345(12):912-913.
28. Emanuel E J, Miller F G. The ethics of placebo-controlled trials—A middle ground. *N Eng J Med* 2001 September 20; 345(12):915-919.
29. Carson J L, Noveck H, Berlin J A, Gould S A. Mortality and morbidity in patients with very low blood counts who decline blood transfusion, *Transfusion* 2002; 42:812-818.
30. Reiner A P. Massive Transfusion. In: Speiss B D, Counts R, and Gould S A, editors. Perioperative Transfusion Medicine. Baltimore: Williams and Wilkins; 1998. p. 351-364.
31. Weiskopf R B, Viele M K, Feiner J, Kelley S, Lieberman J, Noorani M, et al. Human cardiovascular and metabolic response to acute, severe isovolemic anemia. *JAMA* 1998; 279(3):217-221.
32. Wilkerson D K, Rosen A L, Sehgal L R, Gould S A, Sehgal H L, Moss G S. Limits of cardiac compensation in anemic baboons. *Surgery* 1988; 103(6):665-670.
33. Levy P S, Chavez R P, Crystal G J, Kim S J, Eckel P K, Sehgal L R, et al. Oxygen extraction ratio: A valid indicator of transfusion need in a limited coronary reserve? *J Trauma* 1992; 32(6):769-774.
34. Schwartz J P, Ludkowski M J, Segil L J, Miletich D J, Law W R, Gould S A. The influence of coronary stenosis on transfusion need. *Surg Forum* 1993; XLIV:226-228.
35. Moss G S, DeWoskin R, Rosen A L, Levine H, Palani C K. Transport of oxygen and carbon dioxide by hemoglobin-saline solution in the red cell-free primate. *Surg Gynecol Obstet* 1976; 142:357-362.
36. Points to consider on efficacy evaluation of hemoglobin- and perfluorocarbon-based oxygen carriers. Center for Biologics Evaluation and Research. *Transfusion* 1994 August; 34(8):712-713.
37. Fratantoni J C. Red Cell Substitutes: Evolution of approaches for demonstrating efficacy. In: Tsuchida E, editor. Blood substitutes-Present and future perspectives. Switzerland: Elsevier Science S A; 1998. p. 33-39.

What is claimed is:

1. A method of maintaining mean circulating hemoglobin (Hb) levels above 5.0 g/dL in a patient suffering from massive blood loss comprising administering to said patient a polymerized hemoglobin solution in an amount of at least one blood volume of said patient, wherein the administration of the solution avoids vasoconstriction, and renal, pancreatic, gastrointestinal and cardiac dysfunction associated with the administration of unmodified hemoglobin solution when treating massive blood loss.

2. The method of claim 1 wherein the hemoglobin solution is administered in an amount of at least 5 L.

3. The method of claim 1 wherein the administration of the hemoglobin solution maintains arterial pressure above 60 mmHg.

4. The method of claim 1 wherein the hemoglobin solution is administered at a rate of at least about 2 units per minute.

5. The method of claim 1 wherein hemoglobin solution is an acellular solution comprising an essentially tetramer-free, cross-linked, polymerized hemoglobin solution which is substantially free of stroma and other contaminants.

6. A method according to claim 5, wherein the polymerized hemoglobin has a molecular weight distribution of:
   (a) from about 5-30% by weight of polymerized hemoglobin of polymer having a molecular weight of about 128 KDa;
   (b) from about 15-35% by weight of polymerized hemoglobin of polymer having a molecular weight of about 192 KDa; and
   (c) from about 35-75% by weight of polymerized hemoglobin of polymer having a molecular weight of about 256 KDa.

7. A method for treating a human having a hemoglobin concentration below about 7 g/dL as the result of a massive blood loss comprising administering to said human a polymerized hemoglobin solution in an amount above 5 L sufficient to maintain arterial pressure above 60 mmHg.

8. The method of claim 7 wherein hemoglobin solution is an acellular solution comprising an essentially tetramer-free, cross-linked, polymerized hemoglobin solution which is substantially free of stroma and other contaminants.

9. The method of claim 7 wherein the hemoglobin solution is administered in an amount of at least one blood volume of the mammal.

10. The method of claim 7 wherein the administration of the hemoglobin solution maintains a mean circulating hemoglobin level greater than 5.0 g/dL.

11. The method of claim 7 wherein the hemoglobin solution is administered at a rate of at least about 2 units per minute.

12. A method according to claim 7, wherein the polymerized hemoglobin has a molecular weight distribution of:

(a) from about 5-30% by weight of polymerized hemoglobin of polymer having a molecular weight of about 128 KDa;
(b) from about 15-35% by weight of polymerized hemoglobin of polymer having a molecular weight of about 192 KDa; and
(c) from about 35-75% by weight of polymerized hemoglobin of polymer having a molecular weight of about 256 KDa.

13. A method for treating a human having a hemoglobin concentration below about 7 g/dL as the result of a massive blood loss comprising administering to said human a polymerized hemoglobin solution in an amount above 5 L sufficient to maintain arterial pressure above 60 mmHg, wherein the administration of the solution avoids vasoconstriction, and renal, pancreatic, gastrointestinal and cardiac dysfunction associated with the administration of unmodified hemoglobin solution when treating massive blood loss.

* * * * *